US009586982B2

(12) United States Patent
Breuil et al.

(10) Patent No.: US 9,586,982 B2
(45) Date of Patent: Mar. 7, 2017

(54) NICKEL-BASED COMPLEX AND USE THEREOF IN A METHOD FOR THE OLIGOMERISATION OF OLEFINS

(71) Applicants: IFP ENERGIES NOUVELLES, Rueil-Malmaison (FR); UNIVERSITEIT VAN AMSTERDAM, Amsterdam (NL)

(72) Inventors: Pierre-Alain Breuil, Lyons (FR); Pierre Boulens, Lyons (FR); Joost Reek, Amersfoort (NL); Helene Olivier-Bourbigou, Saint Genis-Laval (FR)

(73) Assignees: IFP ENERGIES NOUVELLES, Rueil-Malmaison (FR); UNIVERSITEIT VAN AMSTERDAM, Amsterdam (NL)

( * ) Notice: Subject to any disclaimer, the term of this patent is extended or adjusted under 35 U.S.C. 154(b) by 0 days.

(21) Appl. No.: 14/901,394

(22) PCT Filed: Jun. 26, 2014

(86) PCT No.: PCT/FR2014/051625
§ 371 (c)(1),
(2) Date: Dec. 28, 2015

(87) PCT Pub. No.: WO2014/207393
PCT Pub. Date: Dec. 31, 2014

(65) Prior Publication Data
US 2016/0152647 A1  Jun. 2, 2016

(30) Foreign Application Priority Data
Jun. 28, 2013  (FR) .................................. 13 56271

(51) Int. Cl.
*C07F 9/09* (2006.01)
*C07F 15/04* (2006.01)
*C08F 4/80* (2006.01)
*C07C 2/36* (2006.01)
*B01J 31/18* (2006.01)
*C07C 2/32* (2006.01)

(52) U.S. Cl.
CPC ........... *C07F 15/045* (2013.01); *B01J 31/188* (2013.01); *C07C 2/32* (2013.01); *C07C 2/36* (2013.01); *C08F 4/80* (2013.01); *B01J 2231/20* (2013.01); *B01J 2531/847* (2013.01); *C07C 2531/14* (2013.01); *C07C 2531/22* (2013.01); *C07C 2531/24* (2013.01)

(58) Field of Classification Search
CPC .............. C07C 2/32; C07F 15/04; B01J 31/18
USPC .......................................................... 556/17
See application file for complete search history.

(56) References Cited

PUBLICATIONS

Song et al., Eur. J. lnorg. Chem. 2009, 3016-3024.*
Anagho et al., Angew. Chem. Int. Ed. 2005, 44, 3271-3275.*
International Search report dated Sep. 3, 2014 issued in corresponding PCT/FR2014/051625 application (pp. 1-4).
L. E. Anagho, et al., "Synthesis and Solid-State Structure of a Metal Complex of a Diphosphineimine", Angewandte Chemie International Edition, vol. 44 (Jan. 2005) pp. 3271-3275.
K. Song, et al., "Syntheses Structures, and Catalytic Ethylene Oligomerization Behaviors of Bis(phosphanyl) aminenickel(II) Complexes Containing N-Functionalized Pendant Groups", European Journal of Inorganic Chemistry, vol. 2009, No. 20 (Jul. 2009) pp. 3016-3024.

* cited by examiner

*Primary Examiner* — Porfirio Nazario Gonzalez
*Assistant Examiner* — Kofi Adzamli
(74) *Attorney, Agent, or Firm* — Millen, White, Zelano, Branigan, P.C.

(57) ABSTRACT

The invention describes a novel dissymmetric nickel-based complex and the method of preparation thereof from at least one diphosphinamine ligand B1 of formula $(R^1)(R^{1'})P-N(R^3)-P(R^2)(R^{2'})$, or an iminobisphosphine ligand B2 of formula $(R^3)N=P(R^1)(R^{1'})-P(R^2)(R^{2'})$. The invention also concerns the use of said complex in a method for oligomerisation of olefins.

29 Claims, No Drawings

NICKEL-BASED COMPLEX AND USE THEREOF IN A METHOD FOR THE OLIGOMERISATION OF OLEFINS

The invention relates to a novel family of nickel complexes, and methods of preparation thereof. The invention also relates to the use of said complexes as catalysts in chemical transformation reactions.

PRIOR ART

It is known that nickel-based complexes can be prepared for application in various areas of chemistry, particularly in the area of catalytic transformations such as hydroformylation, hydrogenation, cross coupling, oligomerisation of olefins, etc.

Examples of such complexes include the article C.R. Acad. Sci. 1967, C103-106 and the article *J. Mol. Catal.* A 2001, 169, 19-25 which describe nickel complexes in the presence of monophosphine.

The nickel diphosphinamine complexes described in the prior art are symmetric and prepared using diphosphinamine ligands in which the two phosphorous atoms are carriers of identical aromatic-type groups (Eur. J. Inorg. Chem., 2009, 3016-3024, *Organometallics,* 2001, 20, 4769-4771). For example, patent application WO01/10876 describes nickel diphosphinamine complexes, with the symmetric ligands described being substituted, on the phosphorous, solely by aromatic groups, and used for the polymerisation of ethylene.

These catalytic systems are relatively inactive in the oligomerisation of ethylene and are generally used for the polymerisation of ethylene.

The applicant has discovered a novel dissymmetric nickel complex, prepared from dissymmetric diphosphinamine or iminobisphosphine ligands, in which one of the phosphorous atoms carries at least one non-aromatic group and the other phosphorous atom carries at least one aromatic group. It has been discovered that said complexes, whether or not a solvent is present, exhibit improved activity and selectivity for catalytic transformation reactions, in particular for the catalysis of olefin oligomerisation or dimerisation reactions.

DETAILED DESCRIPTION OF THE INVENTION

Nickel Complex of Formula (I)

A first object of the invention relates to a novel dissymmetric nickel complex of formula (I):

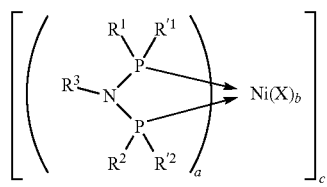

in which
the groups $R^1$ and $R'^1$, which may be identical or different, and may or may not be linked, are selected from the non-aromatic groups,
the groups $R^2$ and $R'^2$, which may be identical or different, and may or may not be linked, are selected from the aromatic groups,
$R^3$ is selected from hydrogen, the halogens, the aliphatic hydrocarbon groups, cyclical or not, and which may or may not contain heteroelements, and the aromatic groups which may or may not contain heteroelements, which may or may not be substituted,
X is an anion or an electron donor, the groups X may or may not be linked, X is selected from hydrogen, the halogens, the aliphatic hydrocarbon groups, cyclical or not, and which may or may not contain heteroelements, which may or may not be substituted, and the aromatic groups which may or may not contain heteroelements, which may or may not be substituted, the olefins, which may or may not contain heteroelements, which may or may not be substituted, the borates, the phosphates, the sulphates, the phosphorous ligands which may or may not contain heteroelements, which may or may not be substituted, the —$OR^4$ or —$N(R^5)(R^6)$ groups, where $R^4$, $R^5$ and $R^6$ are selected from the aliphatic hydrocarbons groups, cyclical, which may or may not contain heteroelements, and the aromatic groups which may or may not contain heteroelements, which may or may not be substituted,
a is a whole number between 1 and 4, b is a whole number between 0 and 6, and c is a whole number between 1 and 4.

The groups $R^1$ and $R'^1$ are preferably selected from the non-aromatic groups and do not contain silicon. $R^1$ and $R'^1$ are preferably identical.

The groups $R^1$ and $R'^1$ are preferably selected from methyl, ethyl, isopropyl, n-butyl, iso-butyl, tert-butyl, pentyl and cyclohexyl groups, which may or may not be substituted.

The groups $R^2$ and $R'^2$ are preferably selected from phenyl, o-tolyl, m-tolyl, p-tolyl, mesityl, 3,5-dimethylphenyl, 4-methoxyphenyl, 2-methoxyphenyl, 2-isopropoxyphenyl, 4-methoxy-3,5-dimethylphenyl, 3,5-di-tert-butyl-4-methoxyphenyl, 3,5-bis(trifluoromethyl)phenyl, benzyl, naphthyl and pyridyl groups, which may or may not be substituted, and may or may not contain heteroelements. $R^2$ and $R'^2$ are preferably identical.

Advantageously, $R^3$ is selected from hydrogen, the alkoxy, aryloxy, sulphur, sulfonamine, sulfonamide, nitro, carbonyl, amino and amido groups which may or may not comprise aliphatic, cyclical or aromatic groups, which may or may not contain heteroelements, which may or may not be substituted.

The complex of formula (I) is advantageously prepared by bringing into contact a nickel precursor A and at least one diphosphinamine ligand B1 of formula $(R^1)(R'^1)P$—N$(R^3)$—P$(R^2)(R'^2)$ or an iminobisphosphine ligand B2 of formula $(R^3)N$=P$(R^1)(R'^1)$—P$(R^2)(R'^2)$ in the presence or not of a solvent, known as a preparation solvent, at a temperature of between −80° C. and +110° C., for a time of between 1 minute and 24 hours.

The nickel precursor A can be selected from nickel(II) chloride, nickel(II)(dimethoxyethane)chloride, nickel(II) bromide, nickel(II)(dimethoxyethane)bromide, nickel(II)fluoride, nickel(II)iodide, nickel(II)sulphate, nickel(II) carbonate, nickel(II)dimethylglyoxime, nickel(II)hydroxide, nickel(II)hydroxyacetate, nickel(II) oxalate, nickel(II)carboxylates such as 2-ethylhexanoate, for example, nickel(II) henates, nickel(II)acetate, nickel(II)trifluoroacetate, nickel (II)triflate, nickel(II) acetylacetonate, nickel(II)hexafluoroacetylacetonate, nickel(0)bis(cycloocta-1,5-diene), nickel (0)bis(cycloocta-1,3-diene), nickel(0)bis (cyclooctatetraene), nickel(0) bis(cycloocta-1,3,7-triene), bis(o-tolylphosphito) nickel(0)(ethylene), nickel(0) tetrakis (triphenylphosphite), nickel(0) tetrakis(triphenylphosphine), nickel (0) bis(ethylene), π-allylnickel(II) chloride, π-allylnickel(II)bromide, methallylnickel(II) chloride dimer, $\eta^3$-allylnickel(II) hexafluorophosphate, $\eta^3$-methallylnickel(II) hexafluorophosphate, and nickel(II)(1,5-cyclooctadiene) in their hydrated or non-hydrated form, used alone or as a mixture. Said nickel precursors may optionally be complexed with Lewis bases.

The preparation solvent can be selected from the organic solvents and preferably from ethers, alcohols, chlorine-containing solvents and saturated, unsaturated, aromatic or non-aromatic, cyclic or non-cyclic hydrocarbons. Said preparation solvent is preferably selected from hexane, cyclohexane, methylcyclohexane, heptane, butane or isobutane, monoolefins or diolefins preferably containing 4 to 20 carbon atoms, benzene, toluene, ortho-xylene, mesitylene, ethylbenzene, dichloromethane, chlorobenzene, methanol and ethanol, pure or as a mixture, and ionic liquids. In the case in which said solvent is an ionic liquid, it is advantageously selected from the ionic liquids described in patents U.S. Pat. No. 6,951,831 B2 and FR 2 895 406 B1.

Preparation of the diphosphinamine ligands B1 of formula $(R^1)(R'^1)P—N(R^3)—P(R^2)(R'^2)$, or iminobisphosphine ligands B2 of formula $(R^3)N=P(R^1)(R'^1)—P(R^2)(R'^2)$ takes place according to methods known from the literature (*Inorg. Chem.* 2003, 2125-2130). The diphosphinamine ligands B1 of formula $(R^1)(R'^1)P—N(R^3)—P(R^2)(R'^2)$ can be prepared and isolated by reacting 1 equivalent of chlorophosphine $Cl—P(R^1)(R'^1)$ and 1 equivalent of chlorophosphine $Cl—P(R^2)(R'^2)$ with a primary or aromatic amine $R^3—NH_2$ in the presence of triethylamine. The iminobisphosphine ligands B2 of formula $(R^3)N=P(R^1)(R'^1)—P(R^2)(R'^2)$ can be prepared and isolated by reacting a primary or aromatic amine $R^3—NH_2$ and 1 equivalent of chlorophosphine $Cl—P(R^1)(R'^1)$ and 1 equivalent of chlorophosphine $Cl—P(R^2)(R'^2)$ introduced one after the other in the presence of triethylamine.

Use of the Complex of Formula (I) in a Chemical Transformation Reaction

The nickel complex of formula (I) according to the invention can be used as a catalyst in a chemical transformation reaction, such as a reaction for hydrogenation, hydroformylation, cross-coupling or oligomerisation of olefins. In particular, the nickel complex of formula (I) is used in a process for oligomerisation of olefins advantageously comprising between 2 and 10 carbon atoms; preferably in a process of dimerisation of ethylene or propylene.

The nickel complex of formula (I) according to the invention can be used in the form of a catalytic composition, in a mixture with a compound C known as an activating agent. Said activating agent is advantageously selected from the group formed by tris(hydrocarbyl)aluminium compounds, chlorine-containing or bromine-containing hydrocarbylaluminium compounds, aluminium halides, aluminoxanes, organo-boron compounds, and organic compounds which are susceptible of donating or accepting a proton, used alone or as a mixture.

The tris(hydrocarbyl)aluminium compounds, the chloride-containing and bromine-containing hydrocarbylaluminium compounds and the aluminium halides preferably adhere to the general formula $Al_xR_yW_z$ in which R represents a monovalent hydrocarbon radical containing for example up to 12 carbon atoms such as alkyl, aryl, aralkyl, alkaryl or cycloalkyl, W represents a halogen atom selected for example from chlorine and bromine, W preferably being a chlorine atom, x takes a value of between 1 and 2, and y and z take a value of between 0 and 3. Examples of compounds of this type which may be mentioned are ethylaluminium sesquichloride ($Et_3Al_2Cl_3$), methylaluminium dichloride ($MeAlCl_2$), ethylaluminium dichloride ($EtAlCl_2$), isobutylaluminium dichloride ($iBuAlCl_2$), diethylaluminium chloride ($Et_2AlCl$), trimethylaluminium, tributylaluminium, tri-n-octylaluminium and triethylaluminium ($AlEt_3$).

In the case in which said activating agent is selected from aluminoxanes, said activating agent is advantageously selected from methylaluminoxane (MAO), ethylaluminoxane and modified methylaluminoxanes (MMAO). These activating agents may be used alone or as a mixture.

Preferably, said activating agent C is selected from dichloroethylaluminium ($EtAlCl_2$) and methylaluminoxane (MAO).

In the case in which said activating agent is selected from organo-boron compounds, said activating agent is preferably selected from Lewis acids of the tris(aryl)borane type, such as tris(perfluorophenyl)borane, tris(3,5-bis(trifluoromethyl)phenyl)borane, tris(2,3,4,6-tetrafluorophenyl)borane, tris(perfluoronaphtyl)borane, tris(perfluorobiphenyl)borane and their derivatives and (aryl)borates associated with a triphenylcarbenium cation, or a trisubstituted ammonium cation such as triphenylcarbenium tetrakis(perfluorophenyl)borate, N,N-dimethylanilinium tetrakis(perfluorophenyl)borate, N,N-diethylanilinium tetrakis(3,5-bis(trifluoromethyl)phenyl)borate, or triphenylcarbenium tetrakis(3,5-bis(trifluoromethyl)phenyl)borate.

In the case in which said activating agent is selected from organic compounds which are susceptible of donating a proton, said activating agent is preferably selected from acids with formula HY in which Y represents an anion.

In the case in which said activating agent is selected from organic compounds which are susceptible of accepting a proton, said activating agent is preferably selected from Brönsted bases.

The nickel complex of formula (I) according to the invention or the catalytic composition containing it is advantageously used in a process of oligomerisation or dimerisation of olefins, preferably in a process of dimerisation of ethylene or propylene.

The solvent for the oligomerisation or dimerisation process may be selected from organic solvents, and preferably from ethers, alcohols, chlorine-containing solvents and saturated, unsaturated, aromatic or non-aromatic, cyclic or non-cyclic hydrocarbons. In particular, said solvent is selected from hexane, cyclohexane, methylcyclohexane, heptane, butane or isobutane, monoolefins or diolefins preferably containing 4 to 20 carbon atoms, benzene, toluene, ortho-xylene, mesitylene, ethylbenzene, dichloromethane, chlorobenzene, methanol and ethanol, pure or as a mixture, and ionic liquids.

In the case in which said reaction solvent is an ionic liquid, it is advantageously selected from the ionic liquids described in patents U.S. Pat. No. 6,951,831 B2 and FR 2 895 406 B1.

Oligomerisation is defined as the transformation of a monomer unit into a compound or mixture of compounds with general formula $C_pH_{2p}$, with $4 \le p \le 80$, preferably with $4 \le p \le 50$, more preferably with $4 \le p \le 26$ and highly preferably with $4 \le p \le 14$.

The olefins used in the oligomerisation or dimerisation process are olefins containing 2 to 10 carbon atoms. Preferably, said olefins are selected from ethylene, propylene, n-butenes and n-pentenes, alone or as a mixture, pure or diluted.

In the case in which said olefins are diluted, said olefins are diluted with one or more alkane(s) such as those found in "cuts" obtained from oil refining processes such as catalytic cracking or steam cracking.

Preferably, the olefin used in the oligomerisation or dimerisation process is ethylene or propylene.

Said olefins may be obtained from non-fossil sources such as biomass. As an example, the olefins used in the oligomerisation process according to the invention may be produced from alcohols, in particular by dehydration of alcohols.

The concentration of nickel in the catalytic solution is advantageously in the range $1 \times 10^{-8}$ to 1 mol/l, and more preferably in the range $1 \times 10^{-6}$ to $1 \times 10^{-2}$ mol/l.

The molar ratio between the activating agent C and the nickel precursor is advantageously between 1/1 and 10,000/1, preferably between 1/1 and 1,000/1 for the aluminoxanes and preferably between 1/1 and 100/1 for the other aluminium derivatives and the other Lewis acids.

The oligomerisation or dimerisation process is advantageously operated at a total pressure in the range between atmospheric pressure and 20 MPa, preferably in the range between 0.5 and 8 MPa, and a temperature in the range −40 to +250° C., preferably in the range −20° C. to 150° C.

The heat generated by the reaction can be eliminated by all means known to a person skilled in the art.

The oligomerisation or dimerisation process can be carried out in a closed system, in a semi-open system or continuously, with one or more reaction stages. Vigorous agitation is advantageously implemented to ensure a good contact between the reagent(s) and the catalytic composition.

The oligomerisation or dimerisation process can be implemented in a discontinuous manner. In this case, the solution comprising the complex according to the invention is introduced into a reactor fitted with the normal agitation, heating and cooling devices.

The oligomerisation or dimerisation process can also be implemented in a continuous manner. In this case, the solution comprising the complex according to the invention is injected at the same time as the olefin into a reactor agitated by conventional mechanical means or by external recirculation, and maintained at the desired temperature.

The catalytic composition is destroyed by any normal means known to a person skilled in the art, then the reaction products and the solvent are separated, for example by distillation. The olefin that has not been transformed can be recycled in the reactor.

The method according to the invention can be implemented in a reactor with one or more reaction stages in series, the olefin feed and/or the catalytic composition pre-conditioned in advance being introduced continuously, either in the first stage, or in the first and any other of the stages. Upon leaving the reactor, the catalytic composition can be deactivated, for example by injection of ammonia and/or an aqueous solution of soda and/or an aqueous solution of sulphuric acid. Unconverted olefins and any alkanes present in the feed are then separated from the oligomers by distillation.

The products of this process may have an application, for example, as components of fuels for motor vehicles, as feeds in a hydroformylation process for the synthesis of aldehydes and alcohols, as components for the chemical, pharmaceutical or perfume industries and/or as feeds in a metathesis process for synthesis of propylene, for example.

The following examples illustrate the invention without limiting its scope. The notation "Cy" represents the tricyclohexyl group.

Example 1

Synthesis of Ligands

Iminobisphosphine ligands R'—SO$_2$—N=P(R$^1$)(R'$^1$)—P(R$^2$)(R'$^2$) were prepared and isolated by reacting a sulfonamide and 2 equivalents of chlorophosphine (which may be identical or different) in the presence of triethylamine. Examples are provided by ligands 1 and 2 in which R$^1$=R'$^1$=R$^2$=R'$^2$ (comparative examples) and ligands 3 and 4 in which R$^1$=R'$^1$ and R$^2$=R'$^2$ and R$^1$ is different from R$^2$. The structures of the four ligands are shown below.

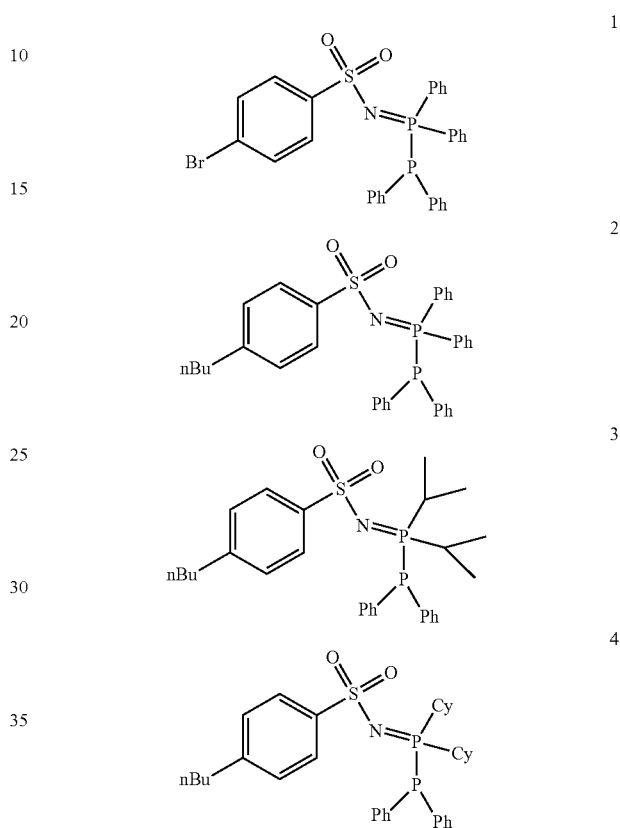

Synthesis of the Ligand 1

(4-Bromo-N-(1,1,2,2-Tetraphenyldiphosphanylidene) Benzenesulfonamide)

Freshly distilled chlorodiphenylphosphine (0.760 ml, 4.24 mmol, 2 eq.) was added drop by drop to a solution of 4-bromobenzenesulfonamide (500 mg, 2.12 mmol, 1 eq.) and triethylamine (1.6 ml, 11.2 mmol, 5.3 eq.) in THF (10 ml) at ambient temperature and under vigorous agitation. Once addition was complete, the mixture was agitated for 5 minutes and then the suspension was filtered under a nitrogen atmosphere on a sintered glass filter. Evaporation of the solvent and the volatile components led to the formation of a solid. This solid was dissolved in a minimum of dichloromethane, then pentane (20 ml) was added. By evaporating this solution, a precipitate appeared. The supernatant was removed using a syringe and the solid was washed with pentane (2×10 ml) and dried under a vacuum to provide ligand 1 in the form of a white powder (isolated yield: 68%).

$^1$H NMR (300 MHz, CD$_2$Cl$_2$): δ 7.82-6.89 (m, 24H). $^{31}$P NMR (121 MHz, CD$_2$Cl$_2$) 19.72 (d, J=281.1 Hz), −18.74 (d, J=281.1 Hz).

$^{31}$P{$^1$H} NMR (121 MHz, CD$_2$Cl$_2$): 19.72 (d, J=279.9 Hz), −18.74 (d, J=281.2 Hz).

MS (FAB+): m/z calc. for C$_{30}$H$_{25}$NO$_2$P$_2$BrS ([MH]$^+$): 606.0248; obs.: 606.0255.

Synthesis of Ligand 2

(4-Butyl-N-(1,1,2,2-Tetraphenyldiphosphanylidene)Benzenesulfonamide)

Freshly distilled chlorodiphenylphosphine (0.840 ml, 4.68 mmol, 2 eq.) was added drop by drop to a solution of 4-butylbenzenesulfonamide (500 mg, 2.34 mmol, 1 eq.) and triethylamine (1 ml, 7.17 mmol, 3 eq.) in THF (20 ml), at ambient temperature and under vigorous agitation. Once addition was complete, the mixture was agitated for 5 minutes and then the suspension was filtered under a nitrogen atmosphere on a sintered glass filter. Evaporation of the solvent and the volatile components led to the formation of an oil. This oil was solubilised in diethyl ether (10 ml) and the solution evaporated. This step was repeated 4 times until the product precipitated. The solid was then dried under a vacuum to provide ligand 2 in the form of a white powder (isolated yield: 79%).

$^1$H NMR (300 MHz, $CD_2Cl_2$): δ 7.91-6.33 (m, —$CH_{Ar}$, 24H), 2.59 (t, $CH_3$—$CH_2$—$CH_2$—$CH_2$—CAr, J=7.7 Hz, 2H), 1.57 (m, $CH_3$—$CH_2$—$CH_2$—$CH_2$—CAr, 2H), 1.33 (m, $CH_3$—$CH_2$—$CH_2$—$CH_2$—Car, 2H), 0.93 (t, $CH_3$—$CH_2$—$CH_2$—$CH_2$—Car, J=7.3 Hz, 3H).

$^{31}$P NMR (121 MHz, $CD_2Cl_2$): δ 19.47 (d, J=277.9 Hz), −17.90 (d, J=278.0 Hz).

MS (FAB+): m/z calc. for $C_{34}H_{34}O_2NP_2S$ ([M+H]$^+$): 582.1786; obs.: 582.1790

Synthesis Of N-Diphenylphosphino-4-Butylbenzenesulfonamide

Freshly distilled chlorodiphenylphosphine (9.38 mmol, 1 eq.) was added drop by drop to a solution of 4-butylbenzene-1-sulfonamide (9.38 mmol, 1 eq.) and triethylamine (25 mmol) in THF (20 ml), at ambient temperature and under vigorous agitation. The suspension was left under agitation for one night at ambient temperature. Evaporation of the solvent and the volatile components led to the formation of a solid. This solid was dissolved in 10 ml of dichloromethane, and then pentane (40 ml) was added, with the appearance of a precipitate. The supernatant was removed using a syringe and the solid was then washed with pentane (2×20 ml) and dried under a vacuum to provide N-diphenylphosphino-4-butylbenzenesulfonamide in the form of a white powder. This compound could be isolated and purified or used directly in another stage of synthesis (isolated yield: 74%).

Synthesis of Ligand 3

4Butyl-N-(1,1-Diisopropyl-2,2-Diphenyldiphosphanylidene)Benzenesulfonamide

Diisopropylchlorophosphine (0.746 ml, 4.68 mmol, 1 eq.) was added drop by drop to a solution of N-diphenylphosphino-4-butylbenzenesulfonamide (1.86 g, 4.68 mmol, 1 eq.) and triethylamine (1.30 ml, 9.36 mmol, 2 eq.) in THF (20 ml), at ambient temperature and under vigorous agitation. Once addition was complete, the mixture was agitated for 10 minutes and then the suspension was filtered under a nitrogen atmosphere on a sintered glass filter. Evaporation of the solvent and the volatile components led to the formation of an oil. Pentane (20 ml) was added to this oil, then following trituration the pentane was removed using a syringe. The oil was then suspended in pentane (10 ml) and the solution evaporated under a vacuum. This step was repeated once with pentane and then twice with diethyl ether (10 ml) allowing the formation of a solid. The solid was washed with pentane (2×10 ml) then dried under a vacuum to provide ligand 3 in the form of a white solid (isolated yield: 34%).

$^1$H (300 MHz, $CD_2Cl_2$): δ: δ 7.98-7.83 (m, 4H, —P$\underline{Ph_2}$), 7.76-7.64 (m, 2H, —$CH_2$—$\underline{Ar}$—$SO_2$), 7.60-7.35 (m, 6H, —P$\underline{Ph_2}$), 7.23-7.12 (m, 2H, —$CH_2$—$\underline{Ar}$—$SO_2$), 2.69-2.57 (t, 2H, J=7.4 Hz, $CH_3$—$CH_2$—$CH_2$—$\underline{CH_2}$—Ar), 2.44 (m, 2H, $CH_3$—$\underline{CH}$—$CH_3$), 1.69-1.48 (m, 2H, $CH_3$—$CH_2$—$\underline{CH_2}$—$CH_2$—Ar), 1.35 (m, 2H, $CH_3$—$\underline{CH_2}$—$CH_2$—$CH_2$—Ar), 1.18-0.99 (m, 12H, $\underline{CH_3}$—CH—$\underline{CH_3}$), 0.93 (t, J =7.3 Hz, 3H, $CH_3$—$CH_2$—$CH_2$—$CH_2$—Ar).

$^{31}$P (121 MHz, $CD_2Cl_2$) δ: 20.13 (d, J=311.6 Hz); 2.80 (d, J=311.6 Hz).

Synthesis of Ligand 4

4-Butyl-N-(1,1-Dicyclohexyl-2,2-Diphenyldiphosphanylidene)Benzenesulfonamide

Dicyclohexylylphosphine (0.200 ml, 0.91 mmol, 1 eq.) was added drop by drop to a solution of N-diphenylphosphino-4-butylbenzenesulfonamide (0.361 g, 0.91 mmol, 1 eq.) and triethylamine (0.126 ml, 1.82 mmol, 2 eq.) in THF (10 ml), at ambient temperature and under vigorous agitation. Once addition was complete, the mixture was agitated for 5 minutes and then the suspension was filtered under a nitrogen atmosphere on a sintered glass filter. Evaporation of the solvent and the volatile components led to the formation of an oil. Pentane (10 ml) was added to this oil, then following trituration it was evaporated under a vacuum. This step was repeated once with pentane and then twice with diethyl ether (10 ml) allowing the formation of a solid. The solid was dried under a vacuum to provide ligand 4 in the form of a white solid (isolated yield: 51%).

$^1$H NMR (300 MHz, $CD_2Cl_2$): δ 7.90 (dd, J =12.5, 7.6 Hz, 4H, P$\underline{Ph_2}$), 7.78-7.67 (dd, J =8.4, 2.0 Hz, 2H, $\underline{Ar}$—$SO_2$), 7.61-7.40 (m, 6H, P$\underline{Ph_2}$), 7.18 (dd, J=8.4, 2.0 Hz, 2H, $\underline{Ar}$—$SO_2$), 2.63 (t, J=7.6 Hz, 2H, —$\underline{CH_2}$—Ar), 2.30-2.01 (m, 2H, $\underline{Cy}$), 1.81 (m, 2H, $\underline{Cy}$), 1.73-1.49 (m, 8H, $\underline{Cy}$), 1.73-1.49 (m, 2H, —$\underline{CH_2}$—$CH_2$—Ar) 1.33 (dt, J=16.3, 7.3 Hz, 2H, —$\underline{CH_2}$—$CH_2$—$CH_2$—Ar), 1.17 (m, 10H, Cy), 0.93 (t, J=7.3 Hz, 3H, $\underline{H_3C}$—$CH_2$—$CH_2$).

$^{31}$P NMR (121 MHz, $CD_2Cl_2$): δ 20.44 (d, J=314.9 Hz), −4.98 (d, J=314.4 Hz).

MS (FAB+): m/z calcd. For $C_{34}H_{34}O_2NP_2S$ ([M+H]$^+$): 594.2725; obsd.: 594.2732.

Synthesis of the Nickel Complexes

The ligands 1, 2, 3 and 4 were reacted with $NiBr_2$(dme) to provide the complexes 5, 6, 7 and 8. Complex 9 is a reference complex.

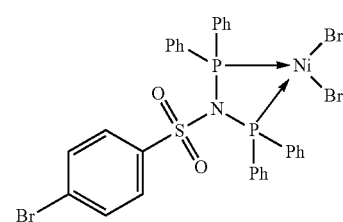

5

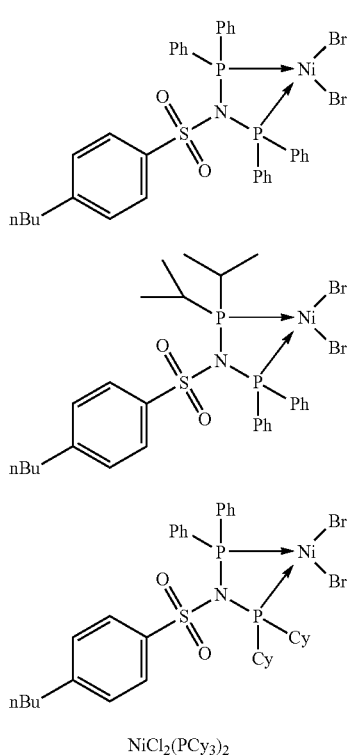

$^{31}$P NMR (121 MHz, CD$_2$Cl$_2$) δ 64.10. $^{31}$P{$^1$H} NMR (121 MHz, CD$_2$Cl$_2$) δ 64.07.

Synthesis of Complex 7

4-butyl-N-(1,1-diisopropyl-2,2-diphenyldiphosphanylidene)benzenesulfonamide 3 (400 mg, 0.786 mmol, 1 eq.) and nickel(II)(dimethoxyethane)bromide (266 mg, 0.864 mmol, 1.1 eq.) were suspended in dichloromethane (5 ml) at ambient temperature for two hours. The solution was filtered on a sintered glass filter and the filtrate evaporated under a vacuum. The solid was washed three times with pentane (10 ml) and dried under a vacuum to provide complex 7 in the form of a red powder (isolated yield: 61%).

$^1$H NMR (300 MHz, CD$_2$Cl$_2$): δ 8.77-6.21 (m, 14H, Ar), 3.29 (m, 4H, CH$_3$—CH—CH$_3$ and —CH$_2$—Ar), 2.43 (m, 2H, CH$_2$—CH$_2$—Ar), 1.66-1.00 (m, 14H, CH$_3$—CH—CH$_3$ and CH$_3$—CH$_2$—CH$_2$—CH$_2$—Ar), 0.78 (t, J=7.8 Hz, 3H, CH$_3$—CH$_2$—CH$_2$—CH$_2$—Ar).

$^{31}$P NMR (121 MHz, CDCl$_3$) δ 116.96 (d, J=119.0 Hz), 62.84 (d, J=119.4 Hz).

$^{31}$P{$^1$H} NMR (121 MHz, CDCl$_3$) δ 116.92 (d, J=116.5 Hz), 62.84 (d, J=117.6 Hz).

Synthesis of Complex 8

4-butyl-N-(1,1-dicyclohexyl-2,2-diphenyldiphosphanylidene)benzenesulfonamide 4 (98 mg, 0.165 mmol, 1.02 eq.) and nickel (II) (dimethoxyethane)bromide (50 mg, 0.162 mmol, 1 eq.) were suspended in dichloromethane at ambient temperature for two hours. The solution was filtered on a sintered glass filter and the filtrate evaporated under a vacuum. The solid was washed three times with pentane (5 ml) and dried under a vacuum to provide complex 8 in the form of a red powder (isolated yield: 54%). Crystals of compound 8 were obtained by slow diffusion of pentane in a solution of 8 in toluene and dichloromethane. The product was analysed by mass, phosphorous NMR and X-ray diffraction.

$^{31}$P NMR (121 MHz, CD2Cl2) δ 108.15 (d, J=118.6 Hz), 60.28 (d, J=119.2 Hz). MS (FAB+): m/z calc. for C$_{34}$H$_{45}$Br$_2$NO$_2$P$_2$SNi ([M]$^+$): 811.0354; obs.: 811.0337.

Synthesis of Complex 5 (Comparative)

4-bromo-N-(1,1,2,2-tetraphenyldiphosphanylidene)benzenesulfonamide 1 (200 mg, 0.331 mmol, 1.01 eq.) and nickel(II)(dimethoxyethane)bromide (101 mg, 0.327 mmol, 1 eq.) were suspended in toluene (3 ml). The suspension was agitated at 60° C. for 2 hours. Following cooling, the solvent was removed using a syringe and the solid washed three times with pentane (5 ml) and then dried under a vacuum to provide complex 5 in the form of a reddish-brown powder (isolated yield: 80%). The product was analysed by mass, proton and phosphorus NMR.

$^1$H NMR (300 MHz, CD$_2$Cl$_2$): δ 8.16 (m, 8H, PPh$_2$), 7.76 (t, J=7.3 Hz, 4H$_{para}$), 7.59 (m, 8H, PPh$_2$), 7.06 (d, J=8.2 Hz, 2H, —Ar—SO$_2$), 6.18 (d, J=8.5 Hz, 2H, —Ar—SO2).

$^{31}$P NMR (121 MHz, CD$_2$Cl$_2$): δ 65.52. $^{31}$P{$^1$H} NMR (121 MHz, CD$_2$Cl$_2$) δ 6 65.52.

MS (FAB+): m/z calc. for C$_{30}$H$_{24}$NO$_2$P$_2$Br$_2$SNi ([M-HBr]$^+$): 741.8701; obs.: 741.8702.

Synthesis of Complex 6 (Comparative)

4-butyl-N-(1,1,2,2-tetraphenyldiphosphanylidene)benzenesulfonamide 2 (200 mg, 0.344 mmol, 1 eq.) and nickel (II)(dimethoxyethane)bromide (106 mg, 0.344 mmol, 1 eq.) were suspended in toluene (3 ml). The suspension was agitated at 65° C. for 1 h until formation of a red solid. Following cooling, the solvent was removed using a syringe and the solid was washed three times with pentane (5 ml) and then dried under a vacuum to provide complex 6 in the form of a reddish-brown powder (isolated yield: 68%). The product was analysed by proton and phosphorous NMR.

$^1$H NMR (300 MHz, CD$_2$Cl$_2$): δ 8.91-5.91 (m, H$_{Ar}$, 24H), 2.72-2.24 (m, CH$_3$—CH$_2$—CH$_2$—CH$_2$—CAr 2H), 1.51 (m, CH$_3$—CH$_2$—CH$_2$—CH$_2$—CAr, 2H), 1.31 (m, CH$_3$—CH$_2$—CH$_2$—CH$_2$—CAr 2H), 0.95 (m, CH$_3$—CH$_2$—CH$_2$—CH$_2$—CAr 3H).

Example 2

Oligomerisation of Ethylene

The ethylene oligomerisation reaction was evaluated with nickel complexes 5 and 6 and 7 in the presence of methylaluminoxane (MAO) at 45° C. and under 30 bar of ethylene (1 bar=0.1 MPa)

Operating conditions: The 100 ml reactor was dried under a vacuum at 100° C. for 2 hours and pressurised with ethylene. The catalyst was introduced (0.1 mmol in 8 ml of toluene) followed by methylaluminoxane (2 ml, 10% in toluene, 300 eq.). The temperature and the pressure were set at 45° C. and 35 bar. Agitation was commenced (t=0). After the set reaction time, the reactor was cooled to ambient temperature and depressurised under agitation. The liquid phase was neutralised with aqueous H$_2$SO$_4$ and analysed by GC.

Complexes 5 and 6 activated by MAO (300 eq.) were considered to be inactive, as the consumption of ethylene was negligible. Complex 7, activated by MAO was highly active in the oligomerisation of ethylene (>10$^7$ g$_{C2H4}$/(mol$_{Ni}$.h)) and no polymer was formed. The GC analyses confirmed that the products formed were principally butenes and hexenes. The results are shown in Table 1.

TABLE 1

Oligomerisation of ethylene catalysed by 5, 6, 7.[a]

| Entry | Complex | Time (min.) | Cons. $C_2H_4$ (g) | Activity[b] | \multicolumn{3}{c}{Distribution by oligomers [wt. %]} | | | 1-$C_4$[d] | 2-$C_4$[d] |
|---|---|---|---|---|---|---|---|---|---|
| | | | | | $C_4$[c] | $C_6$[c] | $C_8^{+c}$ | 1-$C_4$[d] | 2-$C_4$[d] |
| 1[e] | 5 | 22 | N.d.[f] | — | — | — | — | — | — |
| 2[e] | 6 | 20 | N.d.[f] | — | — | — | — | — | — |
| 3 | 7 | 14 | 31.5 | $14.10^6$ | 60.3 | 25.7 | 14.0 | 6.6 | 93.4 |

[a]Reaction conditions: $n_{ni}$ =10 μmol, co-catalyst: MAO (300 eq.), 30 bar $C_2H_4$, 45° C., solvent: toluene (10 ml).
[b]$g_{C2H4}/(mol_{Ni} \cdot h)$.
[c]Determined by GC, wt. %/all oligomers.
[d]wt. %/to the other products of cut C4.
[e]Comparative examples.
[f]Not determined: ethylene consumption negligible, activities observed $<0.7 \cdot 10^6$.

Dissymmetric complex 7 led to performances that were far superior in terms of activity to symmetric complexes 5 or 6.

Example 3

Oligomerisation of Propylene

The oligomerisation of propylene was performed with two different activating agents: EADC (ethylaluminium dichloride) and MAO (methylaluminoxane). The tests performed with catalyst 9 $NiCl_2(PCy_3)_2$ are reference tests.

Tests with EADC

Operating conditions: The 250 ml reactor was dried under a vacuum at 100° C. for 2 hours, cooled to 10° C. and then filled with propylene (pressure of 1.4 bar). 33 ml of chlorobenzene and 10 ml of n-heptane (accurately weighed internal standard) were then introduced, followed by 8 g of propylene. The reactor was cooled to −10° C. under agitation. The EADC (ethylaluminium dichloride, 0.075 M in toluene, 15 eq., 2 ml) activating agent was then injected, followed by the catalyst (0.1 mmol in 5 ml of chlorobenzene). 12 g of propylene were then introduced. Agitation was then commenced (t=0). The temperature was maintained at −10° C. for 10 minutes and then smoothly increased to 10° C. The consumption of propylene was followed by a reduction in pressure. The liquid phase was then removed and neutralised with aqueous NaOH. The organic phase was weighed and analysed by a GC fitted with a cryostat. The results are shown in Table 2.

Following activation with the EADC activating agent, complexes 7, 8 and 9 were highly active for the oligomerisation of propylene at 10° C. The C6 selectivity of complexes 7 and 8 was superior to the reference complex 9. The 1-dimethylbutene and 2-dimethylbutene selectivity was approximately 25% for activated complexes 7 and 8.

TABLE 2

Oligomerisation of propylene with different complexes activated by the EADC activating agent.[a]

| Entry | Complex | Time (min.) | Activity[b] | \multicolumn{4}{c}{Distribution by oligomers [wt. %][c]} | | | |
|---|---|---|---|---|---|---|---|
| | | | | C6 | C9 | C12 | C15+ |
| 1[d] | 6 | 54 | Inactive | | | | |
| 2 | 7 | 30 | 4 | 96.8 | 2.9 | 0.2 | 0.1 |
| 3 | 8 | 5 | 24 | 97.1 | 2.3 | 0.2 | 0.4 |
| 4[d] | 9 | 42 | 2.9 | 86.4 | 12.1 | 1.3 | 0.2 |

[a]Reaction conditions: $n_{ni}$ = 10 μmol, co-catalyst: EADC (15 eq.), 20 g $C_3H_6$, 10° C., solvent: chlorobenzene (50 ml).
[b]$10^6 \; g_{oligo} \cdot mol_{Ni}^{-h} \cdot h^{-1}$.
[c]Determined by GC with n-heptane as internal standard.
[d]Comparative example.

The dimer selectivity obtained with complexes 7, 8 and 9 activated with the EADC activating agent is shown in Table 3.

TABLE 3

| | | \multicolumn{7}{c}{dimer selectivity} | | | | | | |
|---|---|---|---|---|---|---|---|---|
| Entry | Complex | 4M1P | 1-DMB | 4M2P | 2M1P | 2M2P | Hex | 2-DMB |
| 2 | 7 | 1.2 | 23.7 | 35.5 | 13 | 13.4 | 11.4 | 1.8 |
| 3 | 8 | 1.1 | 17.3 | 43.3 | 12.4 | 11 | 13.6 | 1.3 |
| 4[a] | 9 | 6.6 | 62.2 | 10.9 | 17.2 | 0.5 | 2.4 | 0.2 |

Dimer selectivity in wt. %, determined by GC. 4M1P: 4-methylpentene-1, 1-DMB: 2,3-dimethylbutene-1, 4M2P: 4-methylpentene-2, 2M1P: 2-methylpentene-1, 2M2P: 2-methylepentene-2, Hex: linear hexenes, 2-DMB: 2,3-dimethylbutene-2.
[a]Comparative examples.

Tests with MAO

Operating conditions: The 250 ml reactor was dried under a vacuum at 100° C. for 2 hours, cooled to 10° C. and then filled with propylene (pressure of 1.4 bar). 33 ml of chlorobenzene and 10 ml of n-heptane (accurately weighed internal standard) were then introduced, followed by 4 g of propylene. The co-catalyst MAO (1.5 M in toluene, 300 eq., 2 ml) was then injected followed by the catalyst (0.1 mmol in 5 ml of chlorobenzene). 16 g of propylene were then introduced. Agitation was then commenced (t=0). The temperature was maintained at 10° C. for 10 minutes and was then smoothly increased to 45° C. The consumption of propylene was followed by a reduction in pressure. The liquid phase was then removed and neutralised with aqueous $H_2SO_4$. The organic phase was weighed and analysed by a GC fitted with a cryostat. The results are shown in Table 4.

Following activation with MAO, complexes 7, 8 and 9 were active for oligomerisation of propylene at 45° C. The C6 selectivity of complexes 7 and 8 was superior to reference complex 9. The 1-dimethylbutene and 2-dimethylbutene (DMB 1 and 2) selectivity was 40.7% and 47.8% for activated complexes 7 and 8, respectively.

TABLE 4

Oligomerisation of propylene with different complexes activated by MAO.[a]

| Entry | Complex | Distribution by oligomers [wt. %][b] | | | |
|---|---|---|---|---|---|
| | | C6 | C9 | C12 | C15+ |
| 1 | 7 | 81.3 | 12.3 | 3.9 | 2.5 |
| 2 | 8 | 80.1 | 14 | 4.3 | 1.6 |
| 3[c] | 9 | 56.5 | 23.3 | 10.8 | 9.4 |

[a]Reaction conditions: $n_{ni}$ = 10 µmol, co-catalyst: MAO (300 eq.), 10° C., 20 g $C_3H_6$, solvent: chlorobenzene (50 ml), reaction time: 110 min, total conversion.
[b]Determined by GC with n-heptane as internal standard.
[c]Comparative examples.

The dimer selectivity obtained with complexes 7, 8 and 9 activated with MAO activating agent is shown in Table 5.

TABLE 5

Dimer selectivity.

| Entry | Complex | 4M1P | 1-DMB | 4M2P | 2M1P | 2M2P | Hex | 2-DMB |
|---|---|---|---|---|---|---|---|---|
| 1 | 7 | 1.9 | 37.9 | 11.8 | 25.3 | 13.9 | 6.4 | 2.8 |
| 2 | 8 | 1.8 | 44.7 | 7.8 | 25.5 | 12.3 | 4.8 | 3.1 |
| 3a | 9 | 0.6 | 72.8 | 6.3 | 12.9 | 4.1 | 2.4 | 0.9 |

Dimer selectivity in wt. %, determined by GC. 4M1P: 4-methylpentene-1, 1-DMB: 2,3-dimethylbutene-1, 4M2P: 4-methylpentene-2, 2M1P: 2-methylpentene-1, 2M2P: 2-methylepentene-2, Hex: linear hexenes, 2-DMB: 2,3-dimethylbutene-2.
aComparative examples.

The above examples show that the catalytic complexes of the method according to the invention have an improved activity and selectivity for the oligomerisation of olefins comprising preferably between 2 and 10 carbon atoms, more specifically for the dimerisation of olefins comprising between 2 and 10 carbon atoms.

The invention claimed is:

1. A dissymmetric nickel complex of formula (I):

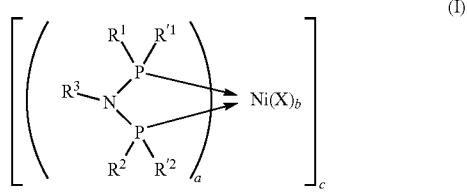

(I)

in which
the groups $R^1$ and $R'^1$, which may be identical or different, and may or may not be linked, are each selected from non-aromatic groups that do not contain silicon,
the groups $R^2$ and $R'^2$, which may be identical or different, and may or may not be linked, are each selected from aromatic groups,
$R^3$ is selected from hydrogen,
halogens,
aliphatic hydrocarbon groups which are cyclical or acyclical and which optionally contain heteroelements, and
aromatic groups which optionally contain heteroelements, and which are unsubstituted or substituted, X is an anion or an electron donor selected from hydrogen,
halogens,
aliphatic hydrocarbon groups which are cyclical or acyclical, which optionally contain heteroelements, and are unsubstituted or substituted,
aromatic groups which optionally contain heteroelements, which are unsubstituted or substituted,
olefins which optionally contain heteroelements and which are unsubstituted or substituted,
borates, phosphates, sulphates, phosphorous ligands which optionally contain heteroelements, and which are unsubstituted or substituted, and
—$OR^4$ or —$N(R^5)(R^6)$ where $R^4$, $R^5$ and $R^6$ are each selected from cyclical aliphatic hydrocarbons groups which optionally contain heteroelements, and aromatic groups which optionally contain heteroelements, and which are unsubstituted or substituted,
wherein if a plurality of X groups are present these X groups may or may not be linked,
a is a whole number between 1 and 4,
b is a whole number between 0 and 6, and
c is a whole number between 1 and 4.

2. A complex according to claim 1, wherein $R^1$ and $R'^1$ are each selected from methyl, ethyl, isopropyl, n-butyl, isobutyl, tert-butyl, pentyl, and cyclohexyl groups that are substituted or unsubstituted.

3. A complex according to claim 1, wherein $R^2$ and $R'^2$ are each selected from phenyl, o-tolyl, m-tolyl, p-tolyl, 3,5-dimethylphenyl, 4-methoxyphenyl, 2-methoxyphenyl, 2-isopropoxyphenyl, 4-methoxy-3,5-dimethylphenyl, 3,5-ditert-butyl-4-methoxyphenyl, 3,5-bis(trifluoromethyl)phenyl, benzyl, naphthyl and pyridyl, which in each case are unsubstituted or substituted and optionally contain heteroelements.

4. A method of preparing a complex according claim 1, comprising:
bringing into contact a nickel precursor A and at least one diphosphinamine ligand B1 of formula $(R^1)(R'^1)P$—$N(R^3)$—$P(R^2)(R'^2)$ or at least one iminobisphosphine ligand B2 of formula $(R^3)N$=$P(R^2)(R'^2)$, optionally in the presence of a solvent,
wherein $R^1$, $R'^1$, $R^2$, $R'^2$ and $R^3$ are as defined in claim 1.

5. The method according to claim 4, wherein the contacting is implemented at a temperature of between −80° C. and +110° C., for a time period of between 1 minute and 24 hours.

6. The method according to claim 4 in which the nickel precursor A is selected from nickel (II) chloride, nickel(II) (dimethoxyethane) chloride, nickel(II) bromide, nickel(II) (dimethoxyethane) bromide, nickel(II) fluoride, nickel(II) iodide, nickel(II) sulphate, nickel(II) carbonate, nickel(II) dimethylglyoxime, nickel(II) hydroxide, nickel(II) hydroxyacetate, nickel(II) oxalate, nickel(II) carboxylates, nickel(II) phenates, nickel(II) acetate, nickel(II) trifluoroacetate, nickel(II) triflate, nickel(II) acetylacetonate, nickel(II) hexafluoroacetylacetonate, nickel(0) bis(cycloocta-1,5-diene), nickel (0) bis(cycloocta-1,3-diene), nickel(0) bis(cyclooctatetraene), nickel(0) bis(cycloocta-1,3,7-triene), bis(o-tolylphosphito) nickel(0)(ethylene), nickel(0) tetrakis(triphenylphosphite), nickel(0) tetrakis(triphenylphosphine), nickel (0) bis(ethylene), π-allylnickel(II) chloride, π-allyl-nickel(II) bromide, methallylnickel(II) chloride dimer, η₃-allylnickel(II) hexafluorophosphate, η³-methallylnickel(II) hexafluorophosphate, and nickel(II) (1,5-cyclooctadiene) in their hydrated or non-hydrated form, used alone or as a mixture, and wherein said nickel precursors are optionally complexed with Lewis bases.

7. A method for oligomerization of olefins comprising bringing said olefins into contact with a complex according to claim 1, and optionally in the presence of a solvent.

8. The method according to claim 7, wherein said complex is used in a mixture with a compound C selected from tris(hydrocarbyl)aluminium compounds, chlorine-containing or bromine-containing hydrocarbylaluminium compounds, aluminoxanes, organo-boron compounds, and organic compounds which are susceptible of donating or accepting a proton, used alone or as a mixture.

9. The method according to claim 7, wherein said olefins are selected from ethylene, propylene, n-butenes, and n-pentenes, used alone or in a mixture, pure or diluted.

10. The method according to claim 7, wherein nickel is present in a concentration of between 1×10⁻⁸ and 1 mol/l.

11. The method according to claim 7, wherein oligomerization is performed at a total pressure in the range between atmospheric pressure and 20 MPa, and at a temperature in the range −40° C. to +250° C.

12. The method according to claim 7, wherein said oligomerization is a dimerization reaction.

13. The method according to claim 12, wherein the reaction is an ethylene or propylene dimerization reaction.

14. A complex according to claim 1, wherein R³ is selected from hydrogen, and alkoxy, aryloxy, sulphur, sulfonamine, sulfonamide, nitro, carbonyl, amino and amido groups which optionally contain heteroelements and which are unsubstituted or substituted.

15. A complex according to claim 1, wherein
R¹ and R¹¹ are each selected from methyl, ethyl, isopropyl, n-butyl, iso-butyl, tert-butyl, pentyl, and cyclohexyl groups,
R² and R¹² are each selected from phenyl, o-tolyl, m-tolyl, p-tolyl, 3,5-dimethylphenyl, 4-methoxyphenyl, 2-methoxyphenyl, 2-isopropoxyphenyl, 4-methoxy-3,5-dimethylphenyl, 3,5-ditert-butyl-4-methoxyphenyl, 3,5-bis(trifluoromethyl)phenyl, benzyl, naphthyl and pyridyl,
R³ is hydrogen, alkoxy, aryloxy, sulphur, sulfonamine, sulfonamide, nitro, carbonyl, amino or amido, and
X in each case is a halogen.

16. A complex according to claim 1, wherein said complex is of the following formula:

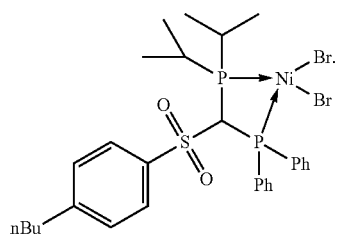

17. A complex according to claim 1, wherein said complex is of the following formula:

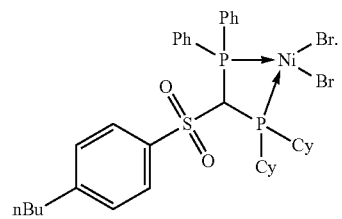

18. The method according to claim 7, wherein said olefins have 2-20 carbon atoms.

19. The method according to claim 8, wherein compound C is selected from ethylaluminium sesquichloride, methylaluminium dichloride, ethylaluminium dichloride, isobutylaluminium dichloride, diethylaluminium chloride, trimethylaluminium, tributylaluminium, tri-n-octylaluminium, triethylaluminium, methylaluminoxane, and ethylaluminoxane.

20. The method according to claim 8, wherein compound C is dichloroethylaluminium or methylaluminoxane (MAO).

21. A complex according to claim 2, wherein R² and R¹² are each selected from phenyl, o-tolyl, m-tolyl, p-tolyl, 3,5-dimethylphenyl, 4-methoxyphenyl, 2-methoxyphenyl, 2-isopropoxyphenyl, 4-methoxy-3,5-dimethylphenyl, 3,5-ditert-butyl-4-methoxyphenyl, 3,5-bis(trifluoromethyl)phenyl, benzyl, naphthyl and pyridyl, which in each case are unsubstituted or substituted and optionally contain heteroelements.

22. A catalyst composition comprising a nickel complex according to claim 1, in a mixture with an activating agent.

23. A catalyst composition according to claim 22, wherein said activating agent is selected from tris(hydrocarbyl)aluminum compounds, chlorine-containing hydrocarbylaluminum compounds, bromine-containing hydrocarbylaluminum compounds, aluminum halides, aluminoxanes, organoboron compounds, and organic compounds which are susceptible of donating or accepting a proton, used alone or as a mixture.

24. A catalyst composition according to claim 22, wherein said activating agent is of the formula $Al_xR_yW_z$ in which R represents a monovalent alkyl, aryl, aralkyl, alkaryl or cycloalkyl radical in each case containing up to 12 carbon atoms, W represents a halogen atom, x is a value of between 1 and 2, and y and z are each independently values between 0 and 3.

25. A catalyst composition according to claim 24, wherein said activating agent is ethylaluminum sesquichloride, methylaluminum dichloride, ethylaluminum dichloride, isobutylaluminum dichloride, diethylaluminum chloride, trimethylaluminum, tributylaluminum, tri-n-octylaluminum and triethylaluminum.

26. A catalyst composition according to claim 22, wherein said activating agent is selected from methylaluminoxane, ethylaluminoxane and modified methylaluminoxanes, used alone or as a mixture.

27. A catalyst composition according to claim 22, wherein said activating agent is selected from dichloroethylaluminium and methylaluminoxane.

28. A catalyst composition according to claim 22, wherein said activating agent is selected from tris(perfluorophenyl)borane, tris(3,5-bis(trifluoromethyl)phenyl)borane, tris(2,3,4,6-tetrafluorophenyl)borane, tris(perfluoronaphtyl)borane, tris(perfluorobiphenyl)borane, triphenylcarbenium tetrakis(perfluorophenyl)borate, N,N-dimethylanilinium tetrakis(perfluorophenyl)borate, N,N-diethylanilinium tetrakis(3,5- bis(trifluoromethyl)phenyl)borate, and triphenylcarbenium tetrakis(3,5-bis(trifluoromethyl)phenyl)borate.

29. A catalyst composition according to claim 22, wherein said activating agent is selected from Brönsted bases.

* * * * *